United States Patent [19]

Zelinka et al.

[11] Patent Number: 4,484,061

[45] Date of Patent: Nov. 20, 1984

[54] TEMPERATURE CONTROL SYSTEM FOR LIQUID CHROMATOGRAPHIC COLUMNS EMPLOYING A THIN FILM HEATER/SENSOR

[75] Inventors: Richard J. Zelinka, Circle Pines; Carl W. Sims, St. Paul, both of Minn.

[73] Assignee: Sys-Tec, Inc., Minneapolis, Minn.

[21] Appl. No.: 377,627

[22] Filed: May 13, 1982

[51] Int. Cl.$^3$ .................. H05B 1/02; G01N 31/08; F16L 53/00; F24H 1/12

[52] U.S. Cl. .................................. 219/301; 73/23.1; 137/341; 138/33; 219/308; 219/311; 219/505; 219/535; 219/543; 219/549

[58] Field of Search ............... 219/296, 301, 504, 505, 219/528, 543, 549, 535, 311, 308; 73/23.1; 222/146 R, 146 H, 146 HE; 138/33; 137/341

[56] References Cited

U.S. PATENT DOCUMENTS

| | | | |
|---|---|---|---|
| 2,274,839 | 3/1942 | Marick | 219/301 X |
| 2,961,522 | 11/1960 | Hammer | 219/543 X |
| 3,043,128 | 7/1962 | Ayers | 73/23.1 |
| 3,063,286 | 11/1962 | Nerheim | 219/301 X |
| 3,125,657 | 3/1964 | Colten | 219/535 |
| 3,225,520 | 12/1965 | Burow | 73/23.1 |
| 3,231,716 | 1/1966 | van den Bosch | 219/535 X |
| 3,296,415 | 1/1967 | Eisler | 219/301 X |
| 3,351,738 | 11/1967 | Kahn | 219/301 |
| 3,355,572 | 11/1967 | Chrow | 219/301 |
| 3,456,096 | 7/1969 | Bilbro | 219/308 X |
| 3,569,665 | 3/1971 | Hager | 219/504 X |
| 4,108,713 | 8/1978 | Weisz | 219/505 X |
| 4,214,147 | 7/1980 | Kraver | 219/301 |
| 4,329,569 | 5/1982 | Hjortsberg et al. | 219/549 X |
| 4,352,707 | 10/1982 | Wengler et al. | 219/528 X |

FOREIGN PATENT DOCUMENTS

| | | | |
|---|---|---|---|
| 2159945 | 7/1972 | Fed. Rep. of Germany | 219/311 |
| 2417233 | 10/1979 | France | 219/301 |

Primary Examiner—A. Bartis
Attorney, Agent, or Firm—Orrin M. Haugen; Thomas J. Nikolai; Douglas L. Tschida

[57] ABSTRACT

A temperature control system for a liquid chromatographic column includes a thin film heater/sensor comprising a foil-like patterned heating element adhesively mounted between a pair of flexible electrically insulative layers. A patterned foil-like temperature sensing element is also coextensively adhesively mounted between the insulative layers in temperature sensing relationship to the heating element. The thin film heater/sensor is wrapped around the chromatographic column and is uniformly compressively secured in contact therewith by a spirally tubularly wound length of flexible wrapping. A remote temperature sensing element controls the heat output of the heating element a linear proportional fashion, thereby maintaining a predetermined temperature gradient over the length of the column. A pre and post-column heaters may be similarly wrapped with a thin film heater/sensors so as to appropriately control the temperature of the liquid entering or leaving the column. The heater/sensor may include a plurality of foil-like patterned heating elements and sensors displaced along the length of the column to define a plurality of heating zones controlled by a patterned foil-like temperature sensing element in sensing relation to respective one of the zones.

7 Claims, 7 Drawing Figures

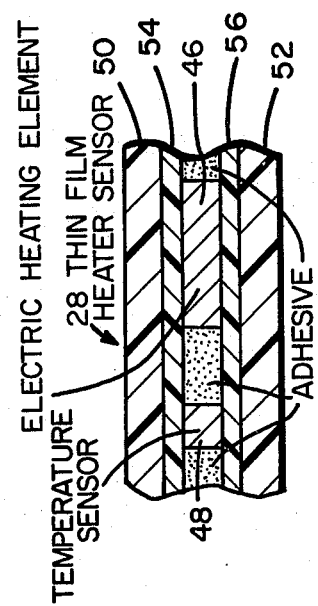
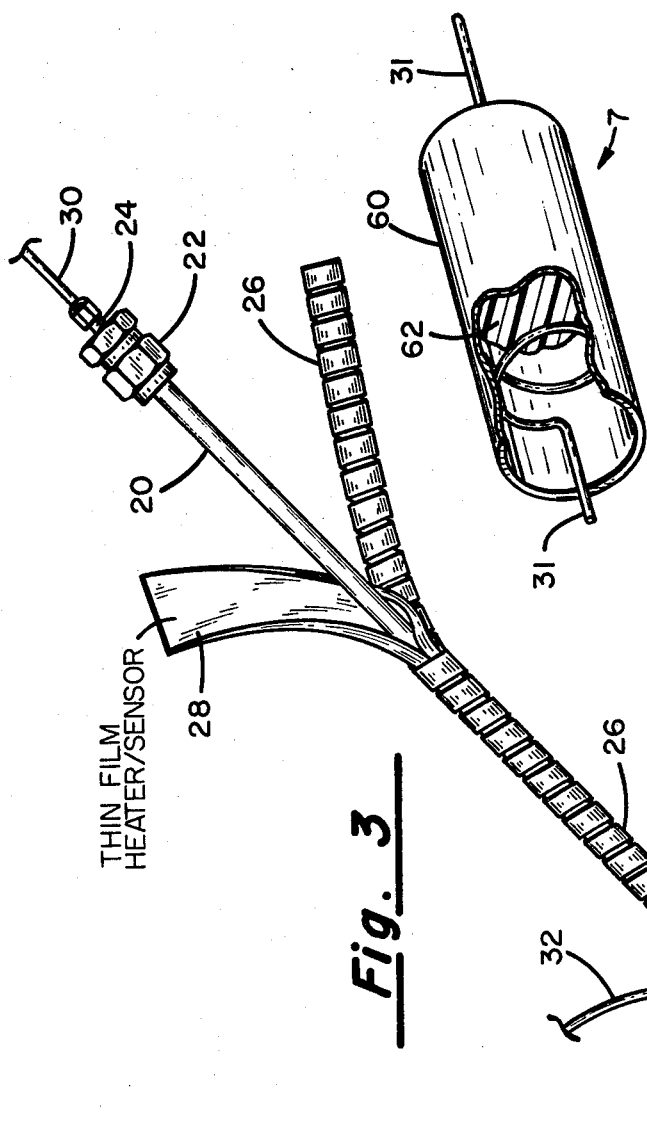
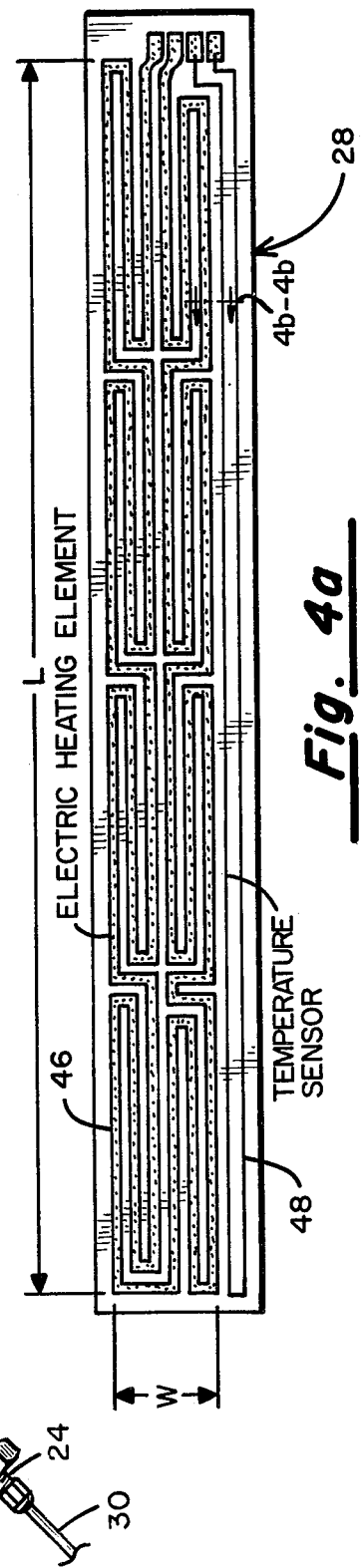

TEMPERATURE CONTROL SYSTEM FOR LIQUID CHROMATOGRAPHIC COLUMNS EMPLOYING A THIN FILM HEATER/SENSOR

BACKGROUND OF THE INVENTION

The present invention relates to temperature control systems and, in particular, to a temperature control system for a liquid chromatography system.

A basic module of a liquid chromatography system is the chromatographic column, sometimes referred to as an HPLC column, through which the sample/solvent flows prior to being detected. Such columns typically comprise a hollow tube that is filled with an appropriate non-reactive adsorbent, such as particles of silica gel, alumina and polyamide, among others. During use and upon injecting a desired volume of a sample into an appropriate solvent, the mixture is forced under pressure through the chromatographic column, where the various compounds of the sample are separated at a rate dependent upon the type of compound, prior to the compounds being sequentially detected by the detector element.

As has long been known, the rate of separation of the compounds is positively affected by the application of heat to the liquid column. Furthermore, by controlling the temperature of the column, the peak retention time reproducibility from sample to sample is dramatically affected, while maintaining a relatively constant baseline or background electrical noise level due to solvent flow in the detector.

Heretofore, temperature controllers employed in conjunction with liquid chromatography systems have been of a water bath, air bath or high mass (e.g. aluminum block) type. The temperature of the surrounding air, water or block in contact with the liquid column is then controlled so as to produce a stable and reproducible temperature gradient over the exterior surface of the chromatographic column. Such temperature controllers, however, suffer from a number of problems, not the least of which are large bulk, high cost, long cooling times, awkward apparatus set-ups and excessively long input and output tubing runs to and from the column.

The present invention, however, presents a low cost alternative temperature control system that essentially does away with all of the above referenced problems. Furthermore, the present invention permits the tailoring of the temperature gradient over the chromatographic column so as to produce either a uniform gradient or a profiled gradient (i.e. uniformly heated solvent/sample) from end-to-end of the column. These objects and advantages are achieved via the use of a temperature controlled thin film heater/sensor that is containably mounted around the column via a spiral retainer and in some instances around a pre-heater and/or post-heater. A temperature controller senses the column surface temperature via a thin film sensor element and appropriately switches power to a thin film heater element so as to maintain the temperature of the column at a uniform, operator selected temperature. Similarly, the pre and post-column heaters are wrapped with appropriate thin film heater/sensors so as to appropriately control the temperature of the liquid flow before and/or after entering and leaving the column. The specific apparatus and its operation, and the above objects and advantages, as well as others, will, however, become more apparent upon a reading of the following description with respect to the following drawings.

SUMMARY OF THE INVENTION

A liquid chromatography temperature control system comprising, in part, a thin film heater/sensor mounted about the chromatographic column. A spiral retainer mounted about the thin film heater/sensor ensures the uniform contacting of the thin film heater/sensor to the chromatographic column, and a temperature controller ensures that a desired temperature gradient is developed from end-to-end along the column. Thus, an appropriate watt density or temperature gradient is developed along the column so as to facilitate the separation and detection of various chemical compounds that are contained in samples that are injected into the solvent flow that passes through the column.

Thin film, pre and post-column heaters are also contemplated, depending upon the type of column and sample. Such heaters are comprised of a thin film heater/sensor wrapped housing that contains an epoxy embedded spiral wound tube passing therethrough.

BRIEF DESCRIPTION OF THE DRAWINGS

FIG. 3 shows a partially assembled perspective view of the present thin film heater/sensor relative to the spiral retainer and chromatographic column.

FIG. 4a shows a typical two dimensional configuration for the thin film heater and sensor elements of the present chromatographic column temperature controller.

FIG. 4b shows a partial cross sectional view taken along lines 4b—4b of FIG. 4a of the various layers of a typical thin film heater/sensor element.

FIG. 5 shows a cutaway, perspective view of a typical pre or post-heater, less its associated thin film heater/sensor.

DESCRIPTION OF THE PREFERRED EMBODIMENT

Figure 1:
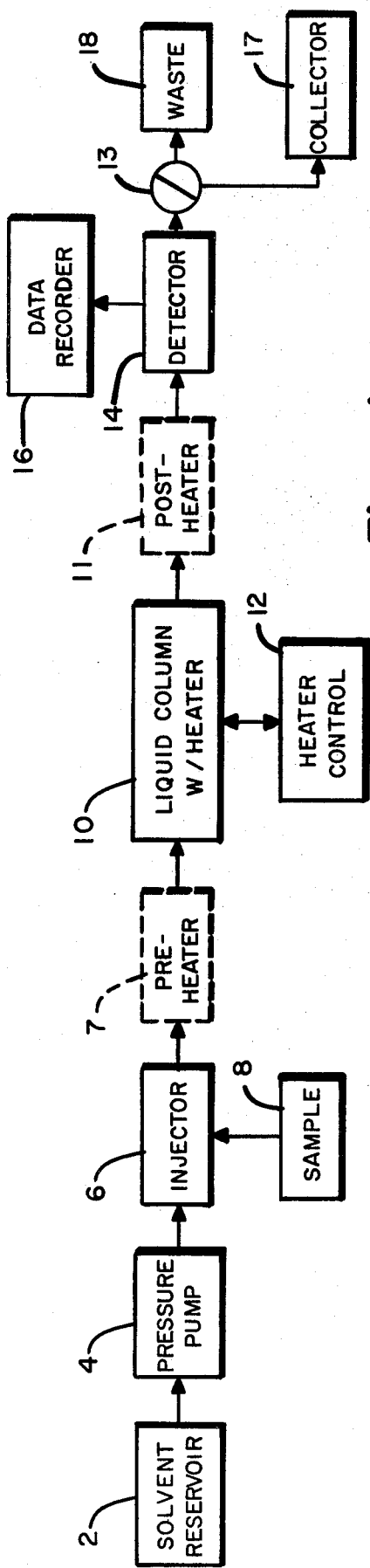
FIG. 1 shows a block diagram of the various elements of a typical liquid chromatograph test station.

The present invention generally comprises an improved temperature control system for a liquid chromatograph test station. Referring to FIG. 1, a generalized block diagram is shown of the various functional elements that are found at a typical liquid chromatograph test station. Generally, and most typically, these elements are a solvent resevoir 2, a pressure pump 4, an injector 6, a sample container or syringe 8, a chromatographic column 10, a heater control 12, a detector 14, a data recorder 16, a sample collector 17 and a waste container 18. In operation, a suitable solvent, selected upon consideration of the sample type and adsorbent material contained within the liquid column 10, is forced to flow via a pressure on the order of 2,000 to 6,000 PSI through the column 10, the detector 14 and into the collector 17 and/or waste container 18, via the valve 13. At appropriate times, a measured volume of a sample material is injected into the solvent stream immediately before the chromatographic column 10, where the compositional compounds of the sample are separated so as to permit the detector 14 and data recorder 16 to detect the solvent/sample flow from the column 10 and display the compositional compounds as a series of varying peak amplitude conditions, with respect to a background or base-line condition for the solvent alone. It is to be recognized though that depending upon the type of detector (i.e. ultra-violet, spectrophotometric, fluorescence, electro-chemical, conductivity, etc.) the separated compounds may be detected and displayed via various other identifying indicators on the recorder 16.

As mentioned, the chromatographic column 10 can be filled with various different types of adsorbing materials; and depending upon the type of adsorbent, size of the tube, flow rate and solvent, the rate at which the separated compounds appear at the detector 14 will vary. Additionally, as the compounds are separated within a relatively cool column 10, they generally exhibit an affinity for the particulate contained within the column. In order to facilitate the separation of the compounds in the column 10, heat is therefore applied to the column 10. Also, by maintaining a constant temperature over the column, the base-line is essentially held constant and which permits an accurate interpretation of the peak conditions mentioned above. Previous methods and apparatus for applying heat to the column 10 have employed liquid baths, air baths and solid mass heater elements. Such temperature controlling systems, however, suffer from a number of problems, as previously mentioned. In an effort to overcome these problems the present invention was designed, and which can be seen upon reference to FIGS. 2 and 5.

Figure 2:
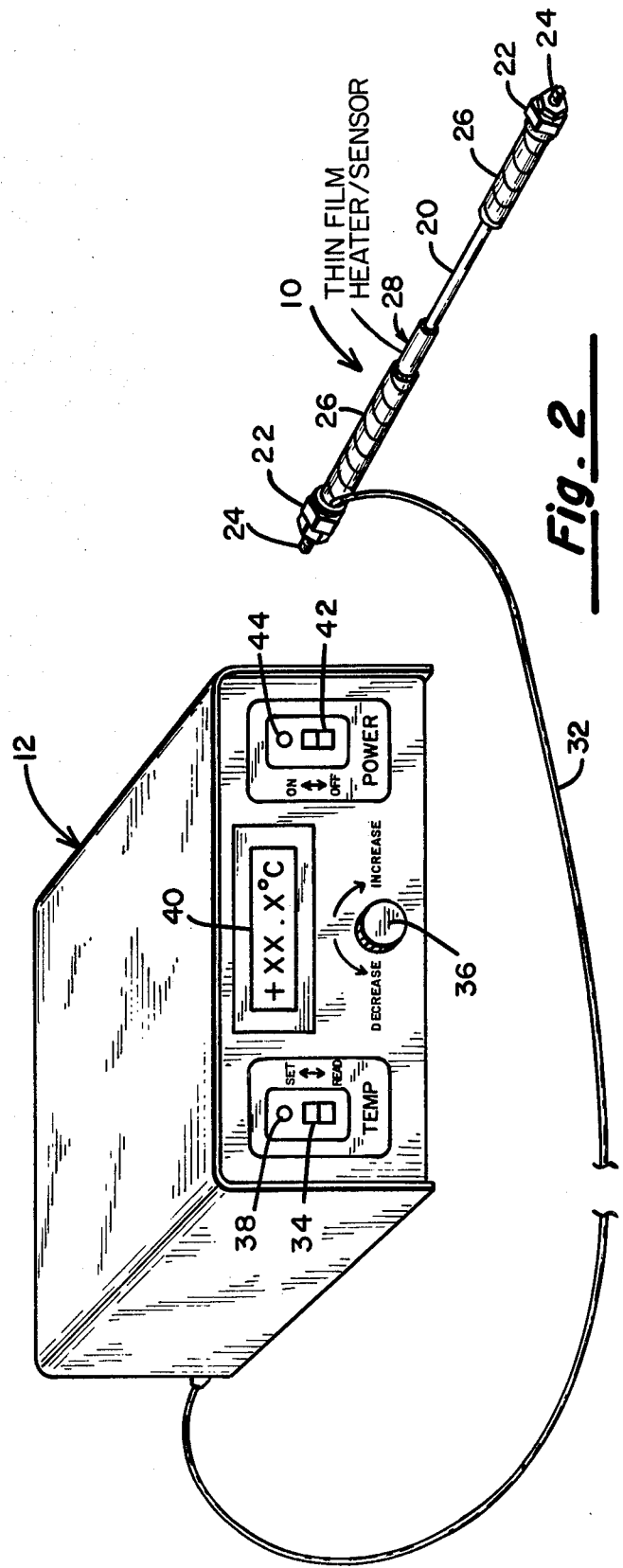
FIG. 2 shows a perspective view of the present chromatographic column temperature controller with respect to a typical chromatographic column.

The apparatus of FIG. 2 essentially comprises the elements labeled "column with heater" 10 and "heater control" 12 of FIG. 1. Referring to the element labeled "column with heater" 10 it is be noted that it essentially is comprised of a chromatographic tube 20 having compression fittings 22 attached to the input and output ends of the tube 20. The compression fittings 22, in turn, contain threaded nipples 24 and to which separate capillary tubes (not shown) couple the input side of the liquid column tube 20 to the injector 6 and the output side to the detector 14. As is generally well recognized, it is desireable to minimize the lengths of such capillary tubes so as to minimize any dead space in the system and within which undesired band broadening or cooling can take place. Such a minimization of the length of the capillary tubes can be achieved with the simplified apparatus of FIG. 2, while also permitting an operator to essentially place the tube 20 in any desired holder, and thereby accommodate the space requirements of most test stations as well as facilitate the operator's testing.

Wrapped about the tube 20 is a spiral retainer 26 having a coextensive lengthwise bore, that is cut to an appropriate length so as to encompass to the entire length of the tube 20 and the windings of which may be unwound but which return to their unflexed shape when released. The unflexed cross-sectional area of said bore being less than that of a thin film heater/sensor 28 wrapped chromatographic tube 20. During assembly a thin film heater/sensor 28 of a matching length to the tube 20 is placed adjacent to the exterior surface of the tube 20 and the spiral retainer 26 is wrapped thereabout so as to contain the thin film heater/sensor 28 in intimate contact at a uniform pressure along the surface of the chromatographic tube 20. The manner of this assembly, however, can better be seen upon reference to FIG. 3, wherein a partially assembled perspective view is shown of the tube 20, the spiral retainer 26, the thin film heater/sensor 28 and the capillary tubes 30.

Referring again to FIG. 2, attached to the thin film heater/sensor 28 is a suitable multiwire conductor 32, whereby power is applied to the heating element(s) of the thin film 28 and temperature is sensed from the sensor element(s) adjacent to the surface of the tube 20. Such conductors will, however, be discussed in greater detail hereinafter.

The heater controller 12 essentially comprises a temperature controller that is compatible with a 200 ohmn sensor element that is contained within the thin film heater/sensor 28; although, it is to be noted that the resistance of the sensor may be any other value and therefore the only requirement is that the controller 12 be compatible therewith. The operation and circuitry of such temperature controllers is however, generally well known in the art, and therefore will not be discussed herein in any detail. An interested reader can however refer to the present assignee's copending U.S. Patent application Ser. No. 06/354,654, filed Mar. 4, 1982 entitled "Constant Current Closed Loop Controller For Rotating System" for additional information relating to a closed loop controllers of this type. Additionally, information can be obtained upon reference to other readily available literature, such as provided with proportional temperature controllers as manufactured by Yellow Springs Instrument Company, for example a Model 72.

Alternatively and generally, it is desired that the controller 12 of the present preferred apparatus be designed so as to be compatible with the 200 ohm sensor element of the thin film heater/sensor 28 so as to ensure a linear relationship between the operator selected temperature and the actual temperature measured across the surface of the tube 20. Additionally, it is desired that the controller 12 offer a temperature control range from ambient to 100° or 150° C., an adjustability in increments of 0.1° C., an absolute temperature accuracy of a plus or minus 0.5° C. over the entire range, a temperature set repeatability of 0.1° C. and a temperature stability of plus or minus 0.1° C. It is to be recognized though that depending upon the type of sensor (i.e. point or averaging), sensor resistance value and application, the pertinent parameters of the controller 12 may be varied as necessary.

From FIG. 2, it should be noted that the controller 12 of the present invention permits the operator to set the desired temperature at which the tube 20 is to be maintained via the momentary rocker arm switch 34. The switch 34 typically rests in its "Read position" so as to permit the operator to read the temperature of the tube 20. However, the switch 34 can be actuated to its "Set position", while the temperature selector 36 is adjusted to either increase or decrease the set temperature. In order to facilitate the setting of the temperature, it is necessary to provide a temperature selector 36 of an appropriate range, such as a ten turn potentiometer, so as to provide enough separation between settings and permit the circuitry of the controller 12 to properly respond to the selectable control range, (e.g. ambient to 100° C.). Adjacent to and above the switch 34, a light emitting diode (LED) 38 indicates the cycling of the controller 12 as it delivers power to the heater element of the thin film heater/sensor 28.

The temperature for the controller 12 is, in turn, displayed via the digital, liquid crystal display (LCD) 40 in degrees and tenths (i.e. +xx.x° C.) over a range of 0 to 100° C., although an LED or any other suitable display may also be used. During a Set operation, the temperature displayed corresponds to the set temperature; whereas during a Read operation, the temperature corresponds to the sensed temperature, via the sensor element of the thin film heater/sensor 28. Finally, a rocker switch 42 serves as an on/off switch and the LED 44 indicates when power is on.

Additionally and not shown, the controller 12 of the present invention contains additional backpanel jacks for enabling the placement of the controller 12 intermediate to the ribbon heater/sensor 28 and a microprocessor or other automatic controller (not shown). Such other controller can then direct the operation of the controller 12 as part of a larger testing procedure, wherein a liquid chromatographic test is but one of many tests. Furthermore, it is to be noted that the controller 12 is transformer isolated and power is delivered via a low voltage DC, closed loop control as the controller 12 tracks the temperature of the tube 20. It should also be noted that while a linear proportional control is desired, a quasi-proportional control is acceptable, since a slight averaging of the sensed temperature over the length of the tube 20 is often times more practical than a truely linear control for the temperature at a point on the tube. A linear proportional temperature is however essentially achieved via the present controller 12 for the smaller, shorter length chromatographic tubes 20 (i.e. 4.6 millimeters inside diameter and 25 centimeters length).

Figure 4C:
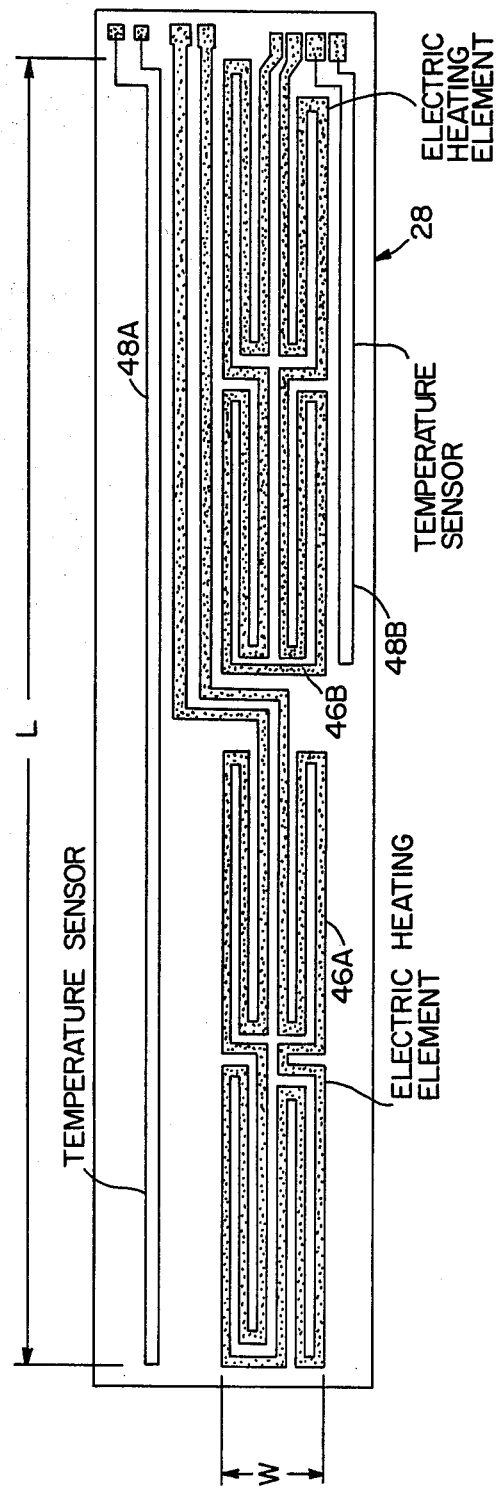
FIG. 4c shows a plan view of a multi-zoned thin film heater.

In order to ensure a uniform watt density or temperature gradient over the entire length of the tube 20, it is necessary that the controller 12 be able to cycle at a high rate and supply sufficient power with each cycle so as to maintain the desired temperature. For the present apparatus, the temperature is maintained via the thin film heater/sensor 28. The thin film heater/sensor 28 is essentially comprised of a thin film or so called "ribbon" that, in turn, contains a heating element 46 and an adjacent sensor element 48. The thin film heater/sensor 28, can be seen more clearly upon reference to FIGS. 4a and 4b. In particular and with reference to FIG. 4a, one possible pattern for the heater element 46 and the sensor element 48 can be seen. Generally, the heater element 46 comprises a patterned thin film metal (i.e. stainless steel, tungsten, cupro-nickel, et al); and depending upon the tube 20 for which the heater/sensor 28 is intended, the pattern, the thickness of the foil and the width W and length L of the heater element 46 are selected and designed to be compatible. Where a sensor element 48 is needed, the width of the thin film is adjusted to accommodate the sensor element 48.

While the pattern of the heater element 46 represents a desired pattern, it is to be recognized that many others are possible. The primary concern, is that the pattern be such as to provide a maximum area of contact between the heater element 46 and the tube 20, such as in the present multiply redundant design. The present pattern for the heater element 46 essentially provides a symmetrical closed loop path that repeats itself on opposite sides of the tube 20, and which provides the desired maximum contact area. The pattern of FIG. 4a in conjunction with the present controller 12 has also been determined to provide adequate heating for tubes 20 of different materials, and different sizes, such as glass and stainless steel tube 20 from 0.5 millimeters to 25.4 millimeters inside diameter and 75 to 500 millimeters in length. An additional advantage of the present thin film heater/sensor 28 is that a rapid cool-down is also achieved, since there is essentially no mass to the heater, and thus during the usual final solvent rinse step the tube 20 cools rapidly, and which is not the case for high-mass heaters.

Alternatively, for larger tubes or where it is desired to vary the watt density or temperature gradient from end-to-end of the tube 20, a profiled heating arrangement can be used. For example, more than one heater element 46 and sensor element 48 can be employed in the fashion of FIG. 4c and wherein two heater elements 46a and 46b are combined with a pair of sensor elements 48a and 48b. Similarly, additional heater elements 46 and/or associated sensor elements 48 might be formed along the length L of the thin film heater/sensor 28. In operation power would be applied in a stepped or time phased relationship relative to the individual heater elements 46 so as to ensure either a uniform or profiled watt density from end-to-end of the tube. In particular, a profiled watt density offers advantages in that the application of a high watt density at the input end of tube 20 and a lower watt density at the output end ensures that the solvent/sample is uniformly heated as it passes through the tube 20, rather than merely ensuring a uniform watt density from end-to-end of the tube 20. As should be apparent, such watt densities and resulting temperature gradient profiles are of more concern with larger sized tubes 20, rather than with the smaller tubes. However, the present apparatus is clearly adaptable to such situations by the modification thereof to provide for multiple or profiled heat zones and/or the delivery of time phased power thereto.

Integrally mounted adjacent to the closed loop heater element 46 and in temperature sensing communication therewith is a closed loop sensor element 48. For the preferred embodiment, the sensor element is fabricated from a nickel iron (NiFe) wire having a 200 ohmn resistivity at 25° C. Thus, when power is applied to the heater element 46, and as the tube heats up, the resistance of the sensor element 48 varies, and the changes are monitored by the controller 12 relative to the set temperature so as to maintain the temperature on the tube 20 at or near the set temperature. Circuitry of the type for performing such a function can be seen upon reference to the present assignee's earlier referenced co-pending U.S. Patent Application. It should also be noted that for the present circuitry, temperature averaging is employed over the length of the tube 20, however, a finer control can be achieved via redundant circuitry that samples and/or controls the temperature in shorter segments at a correspondingly faster rate.

Next, referring to FIG. 4b, a cross sectional view taken along lines 4b—4b of FIG. 4a is shown through the various layers of the thin film heater/sensor 28. In particular, the thin film heater/sensor 28 comprises a multi-layer structure having upper and lower polyimide films 50 and 52, such as manufactured by the DuPont Company under the name of Kapton ® film, upper and lower Teflon films 54 and 56, and a center foil layer 58 containing the patterned heater 46 and sensor 48. The Teflon films 54 and 56 bond the foil 58 to the polyimide films 50 and 52.

Finally, referring to FIG. 5 and recognizing the desirability of accurately controlling the temperature profile for the solvent/sample, a low dead volume, high watt density pre-heater 7 or post-heater 11 of the type shown in dashed lines in FIG. 1 is shown. In particular, FIG. 5 shows the construction of a pre-heater 7, but it is to be recognized that the construction of the post-heater 11 would be essentially the same. The basic assembly for such heaters comprises a tube-like housing 60 that contains a spiral wound inner capillary tube 31 and an epoxy encapsulant 62. Such assemblies during use, are then combined with their own thin film heater/sensors 28 (wrapped around the housing 60), and which combined assemblies permit the operator to control the temperature of the solvent/sample at the input or output to the tube 20. In test stations employing such heaters, 7 or 11 separate control lines are then typically coupled to the heaters 7 or 11 to control the watt densities thereof and thus temperature of the solvent/sample at the tube 20 and/or at the detector 14. In essence, the appropriate thermal drift of the solvent/sample is thereby minimized and thus a controlled temperature profile is achieved. It is also to be noted that the pre and post heaters 7 and 11 are readily adaptable to test stations using plastic chromatographic columns, such as the Z-Model ™ systems manufactured by Waters Associates, Milford, Mass.

While the present invention has been described with respect to its preferred embodiment as well as with respect to numerous modifications thereof, it is to be recognized that yet still other modifications and equivalent structures may suggest themselves to those of skill in the art upon a reading hereof or upon exposure to the present apparatus. Therefore, it is contemplated that the above described and hereinafter claimed invention includes all those equivalent structures within the scope of the following claims.

What is claimed is:

1. A temperature control system for a chromatographic column comprising in combination:
    a first thin film heater for removable wrap mounting about an exterior surface of a chromatographic column, comprising a foil-like patterned heating element adhesively mounted between upper and lower flexible, electrically insulative layers and including a patterned foil-like temperature sensing element integrally coextensively mounted in temperature sensing relation to said heating element;
    retainer means coextensive with said thin film heater for removably compressively securing said thin film heater and the chromatographic column in heat transfer relation; and
    temperature control means responsively coupled to said sensing element for controlling the watt density applied to said heating element in a linear proportional fashion, thereby maintaining a predetermined temperature gradient over the length of the chromatographic column.

2. A temperature control system as set forth in claim 1 wherein said first thin film heater includes a plurality of integrally mounted, patterned, foil-like heating elements displaced along the length of said thin film heater and at least one patterned, foil-like sensing element mounted in temperature sensing relation to one or more of said plurality of heating elements and wherein said temperature control means controls the watt density applied to each of said plurality of heating elements to maintain a predetermined temperature profile over the length of said chromatographic column.

3. A temperature control system as set forth in claim 1 including a pre- or post-heater comprising:
    a tubular housing having a bore and including a tubular member mounted in said bore and adapted to be connected in fluid flow relation to the chromatographic column;
    a second thin film heater substantially the same as said first thin film heater and mounted in heat exchange relation to said tubular housing and said tubular member; and
    second means responsively coupled to the temperature sensing element of said second thin film heater for controlling the watt density applied to said second thin film heater, whereby the temperature of a substance under test is controlled prior to entering the column or after leaving the column so as to minimize the thermal drift of the liquid therein.

4. A temperature control system as set forth in claim 3 wherein the bore of said tubular housing is filled with a thermally conductive material in heat transfer relation to said housing and said tubular member.

5. A temperature control system as set forth in claim 1 wherein said retainer means comprises a spirally tubularly wound length of flexible wrapping, the windings of which may be unwound but which return to their unflexed shape when released, having a cross-sectional bore area less than that of a thin film heater wrapped column for uniformly compressively securing the wrapped thin film heater to the chromatographic column upon wrapping said retainer means therearound.

6. A temperature control system for a liquid chromatographic column comprising in combination:
    a thin film heater for removable wrap mounting about the exterior surface of a liquid chromatographic column, comprising at least one foil-like patterned heating elements adhesively mounted between upper and lower flexible, electrically insulative layers and including at least one patterned foil-like temperature sensing element integrally coextensively mounted in temperature sensing relation to said at least one heating element:
    retainer means comprising a spirally tubularly wound length of flexible wrapping, the windings of which may be unwound but which return to their unflexed shape when released, having a cross-sectional bore area less than that of a thin film heater wrapped column for uniformly compressively securing the wrapped thin film heater in heat transfer relation to the liquid chromatographic column; and
    means responsively coupled to said at least one sensing element for controlling the watt density applied to said at least one heating element in a linear proportional fashion, thereby maintaining a predetermined temperature profile over the length of said column.

7. A temperature control system comprising in combination:
    a thin film heater for removable wrap mounting about the exterior surface of a member to be heated, comprising a foil-like patterned heating element having a plurality of heating zones adhesively mounted between upper and lower flexible, electrically insulative layers and including a plurality of patterned foil-like temperature sensing elements integrally coextensively mounted in coplanar and temperature sensing relation to respective ones of said heating zones;
    retainer means comprising a spirally tubularly wound length of flexible wrapping the windings of which may be unwound but which return to an unflexed shape when released, having a cross-sectional bore area less than that of said member when wrapped with said thin film heater for uniformly compressively securing the wrapped thin film heater to the member upon wrapping said retainer means therearound; and means responsively coupled to each of said plurality of temperature sensing elements for controlling the watt density applied to each of said plurality of heating zones in a linear proportional fashion, thereby maintaining a predetermined temperature gradient over the length of said member.

* * * * *